US00PP09820P

United States Patent [19]

De Meyer

[11] Patent Number: Plant 9,820

[45] Date of Patent: Mar. 4, 1997

[54] GUZMANIA PLANT NAMED 'RED PEARL'

[75] Inventor: Henri De Meyer, Laarne, Belgium

[73] Assignee: H. De Meyer - De Rouck b.v.b.a., Laarne, Belgium

[21] Appl. No.: 544,823

[22] Filed: Oct. 18, 1995

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new and distinct cultivar or Guzmania plant named 'Red Pearl', characterized by its multi-color bracts terminating in orange-red tips, primarily dark green lower leaves, leaf sheaths which have a fine purple striaten pattern on the bottom surface, and by its long-lasting bract color.

2 Drawing Sheets

The present invention comprises a new and distinct cultivar of *Guzmania squarrosa* referred by the cultivar name 'Red Pearl.' The genus Guzmania is within the family Bromeliaceae.

'Red Pearl' is a product of a planned breeding program conducted in Laarne, Belgium by the inventor Henri De Meyer. The program evolved from the importation by the inventor of seeds of several different cultivars of *Guzmania squarrosa* from Ecuador. When grown out to flower, several plants were selected for their beautiful flowers, and were subsequently crossed with plants of the species *Guzmania lingulata.*

In the hybridization by the inventor in Laarne, Belgium, the female parent was a plant of the *Guzmania lingulata* species identified as "red." The male parent of 'Red Pearl' was an unnamed plant of the *Guzmania squarrosa* species.

'Red Pearl' was discovered and selected by the inventor after flowering in early 1989. The new cultivar was thereafter asexually reproduced from offshoots under the supervision of the inventor in a controlled environment in Laarne, Belgium. The offshoots were rooted, with the resulting plantlets being detached from the mother plant and potted up in an appropriate growing mixture.

Horticultural examination of plants so propagated has demonstrated that the combination of characteristics as herein disclosed for 'Red Pearl' are firmly fixed and retained through successive generations of asexual reproduction, which can be effected by offshoots as described, or by known tissue culture techniques. The new cultivar cannot be propagated from its own seed.

'Red Pearl' has not been observed under all possible environmental conditions. The phenotype may vary significantly when grown under different conditions of temperature, light, and other determining factors, without, however, any variation in genotype. The following observations, measurements and comparisons describe plants grown in Laarne, Belgium under greenhouse conditions which approximate those generally used in commercial practice.

The following traits have been repeatedly observed and are determined to be basic characteristics of 'Red Pearl' which in combination distinguish this Guzmania as a new and distinct cultivar:

1. The inflorescence of 'Red Pearl' has multi-color bracts. Bracts on top of the inflorescence vary from yellow-grown to light green at the sheaths to orange and a more orange-red tip, whereas the bottom bracts have a green top and a red colored lower half.

2. The lower leaves are primarily dark green in color and provide excellent contrast with the sturdy flower cone.

3. The color of the bracts is very long lasting, over six months.

4. The fully grown leaf sheaths are well formed and closely linked at the base. The leaves are green with the sheaths being light yellow-brown to light green. Where the sheaths merge into leaves, a purplish pattern can be found at the bottom side of the leaves, which disappears slowly when reaching half of the length of the leaves. This purplish pattern can best be found on the center (youngest) leaves, closest to the flower stalk.

The accompanying photographic drawings show the inflorescence and foliage characteristics of 'Red Pearl' as clearly as possible. The photo on the first sheet comprises a view of a substantial part of 'Red Pearl' in bloom. The photo on the second sheet comprises a more detailed view of the inflorescence. The colors are as nearly true as possible with color reproduction of this type.

Guzmania 'Red Pearl' can be compared in certain respects to the Guzmania cultivar 'Tutti Frutti', disclosed in U.S. Plant Pat. No. 8,717. The overall shaped of the respective cultivars is very similar. However, bract coloring is distinctly different. The inflorescence of 'Red Pearl' is more red and characterized by a orange-red tip, while the inflorescence of 'Tutti Frutti' is basically orange-red. This makes 'Red Pearl' easily distinguishable from 'Tutti Frutti.'

In the following description, color references are made to The Royal Horticultural Society Color Chart. The color values were determinated in Laarne, Belgium.

Classification:

*Botanical.*—Guzmania hybrid cv. 'Red Pearl'.

Plant:

*Form.*—Rosette.

*Height.*—About 55 cm. when in bloom. The leaf rosette has a height of about 45 cm.

*Diameter.*—Approx. 85–100 cm. when the plant is in bloom.

*Growth habit.*—Stemless.

*Method of propagation.*—By off-shoots or tissue culture.

Foliage:

*Quantity.*—Some 22 to 25 leaves form a close rosette.

*Size.*—The fully grown leaves have a width of about 5.5 cm. and have a length of 60 cm.

*Shape.*—Linear with a pointed tip curling outwards.

*Surface texture.*—The leaf surface is slightly ribbed and shiny, both top and bottom surfaces.

*Color.*—The top surface is closest to but somewhat darker than 147A, and the bottom surface is the same color.

*Leaf sheaths.*—Well formed and closely linked at the base, having a length close to 16 cm. up to the narrowing, and a width up to 10 cm. The newest leaves (in the center of the rosettes) bear a fine purple striped pattern on the bottom surface, thereby making these leaves look darker. The fine purple stripes can also be found on the leaf sheaths of older leaves, but are much less expressive.

Bracts:

*Quantity.*—Some 17–20 bracts are regularly spread along the length of the inflorescence, while about 5 bracts (center bracts), very close to one another, form the top of the inflorescence.

*Size.*—Bracts at the bottom of the flower shaft have a length of about 40 cm. and a width of about 4 cm. Bracts near the top of the flower shaft (except the center bracts) have a length of 10 to 15 cm. and a width of 6 cm. at the base. Bracts are about 2.5 times longer than their width for the upper half of the inflorescence.

*Shape.*—At approximately ⅓ of the length from the top of the bracts, the leaf blade (bract) curls outwards.

*Color.*—The bracts at the bottom of the inflorescence vary in color but all have a green tip. The bottom side is red-pink to purple-red (RHS 52A-55AA), with the base being somewhat lighter, while the upper side is darker (RHS 52l A-B), and also somewhat lighter at the base. The bracts in the middle of the inflorescence start with a yellow-brown to light green color at the base while the main color is red, close to RHS 43A. Approaching the tips, the color changes to RHS 50A-52A, with the tips being dark brown (RHS 200A). The bracts at the top of the inflorescence are a mixture of orange and red as clearly shown in the photographs, and it is difficult to provide an accurate color value or values. The same applies to the bases of the center bracts which are yellow-brown to light green. The bracts keep their color for about 6 months.

Flowers:

*Borne.*—About 15 head-like sub-flower systems are separately embedded in the axils of one of the top bracts. Individual flowers cling to a fibrous receptacle.

*Blooming habit.*—Flowers bloom approximately 16 weeks after induction. Single flowers bloom only one day, and the total inflorescence (from first to last flower) lasts approximately 12 weeks.

*Quantity.*—About 16 to 21 single flowers in each sub-flower system.

*Size.*—The entire flower system (all sub-flowers together which are part of the inflorescence) has a length of 15–20 cm. and a diameter of about 6–7 cm. One sub-flower system has a length of 4.5 cm and a width of 3 cm. Each individual flower is about 4.5–5 cm. in length.

*Shape.*—Straight in the sub-flower system.

*Color.*—The bract of each flower has some red at the top but is mainly yellow-green. (Somewhat lighter than RHS 151A).

*Sepals.*—Three in number; fasciated at the base and membranous (RHS 4D in color); each sepal has a length of approximately 2 cm. and a width of approximately 3 mm.

*Petals.*—Three in number, fasciated with each other and with the 6 stamens. The petals have a length of approximately 2.5 cm. and a width of approximately 4 mm. The color is RHS 12A.

*seed capsule*: A reddish brown pyxidium of about 3 cm. is formed.

*Reproductive organs.*—One pistil and 6 stamens, typical for the species.

It is claimed:

1. A new and distinct cultivar of Guzmania plant named 'Red Pearl', as illustrated and described.

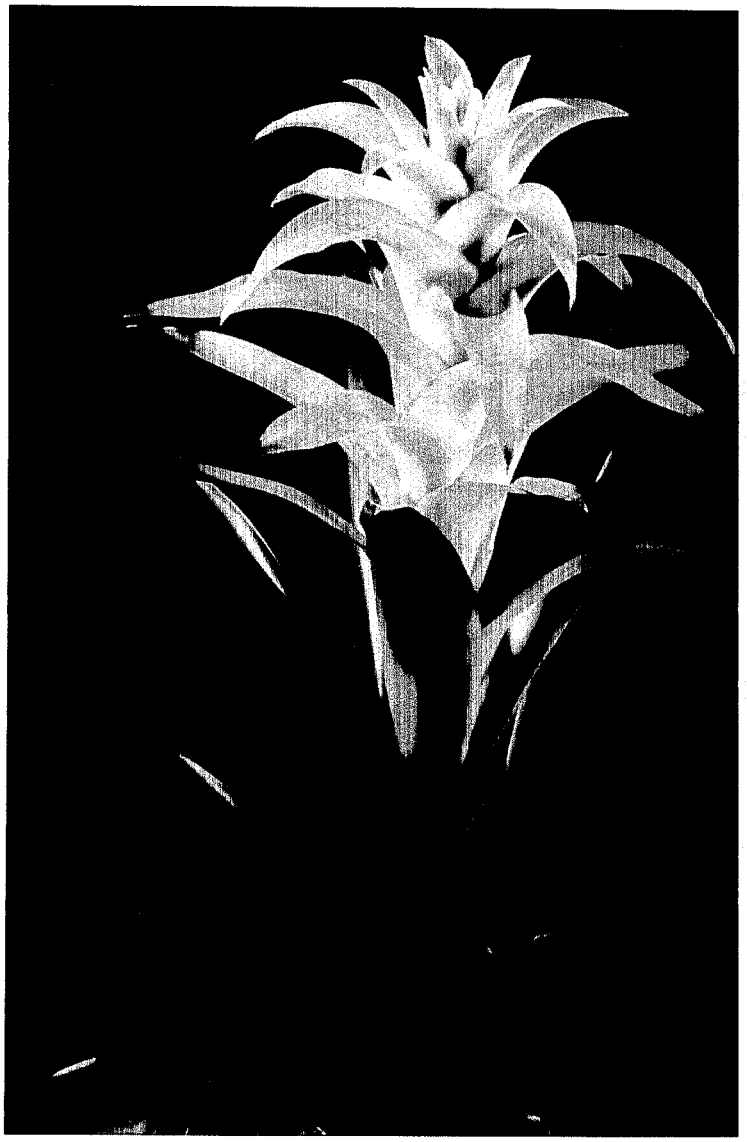

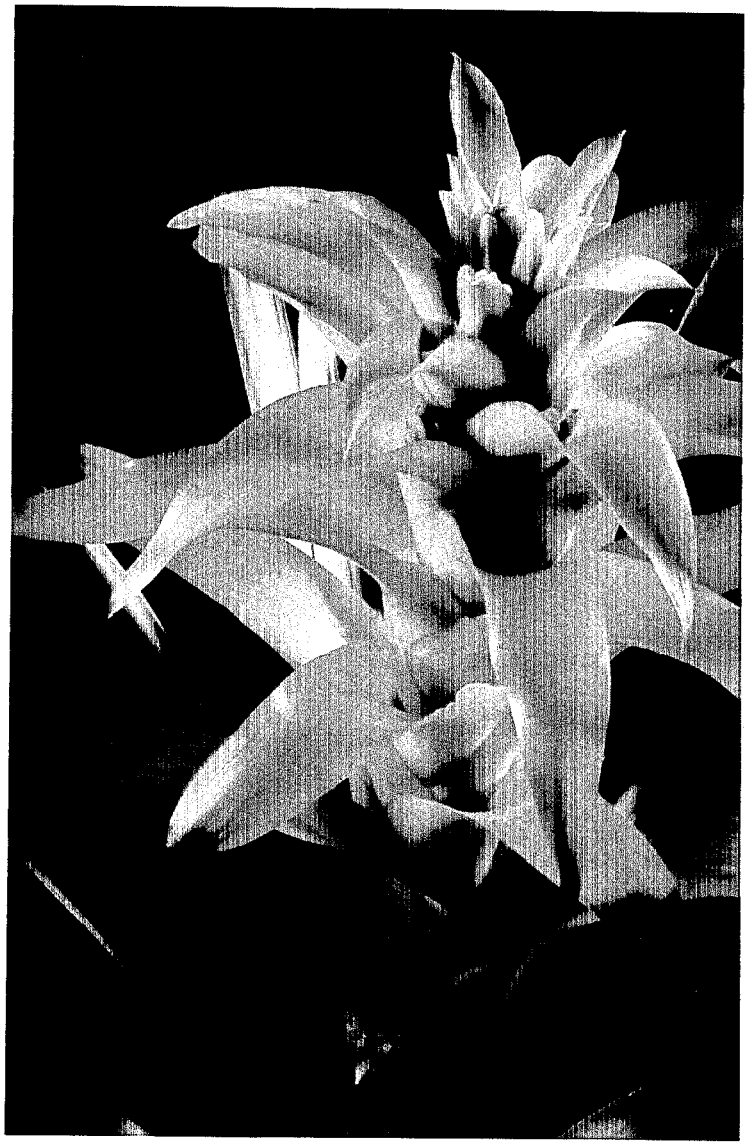

* * * * *